(12) United States Patent
Leban et al.

(10) Patent No.: US 7,071,355 B2
(45) Date of Patent: Jul. 4, 2006

(54) COMPOUNDS AS ANTI-INFLAMMATORY, IMMUNOMODULATORY AND ANTI-PROLIFERATORY AGENTS

(75) Inventors: Johann Leban, Germering (DE); Martin Kralik, Munich (DE)

(73) Assignee: 4 SC AG, Martinsried (DE)

( * ) Notice: Subject to any disclaimer, the term of this patent is extended or adjusted under 35 U.S.C. 154(b) by 0 days.

(21) Appl. No.: 10/736,711

(22) Filed: Dec. 17, 2003

(65) Prior Publication Data

US 2004/0176458 A1    Sep. 9, 2004

Related U.S. Application Data

(60) Provisional application No. 60/435,258, filed on Dec. 23, 2002.

(51) Int. Cl.
C07C 61/20  (2006.01)
C07C 61/22  (2006.01)
A61K 31/20  (2006.01)

(52) U.S. Cl. ............... 562/503; 562/622; 514/563
(58) Field of Classification Search ............... 562/503, 562/504, 622; 514/563
See application file for complete search history.

(56) References Cited

U.S. PATENT DOCUMENTS

| | | | |
|---|---|---|---|
| 3,465,001 A | 9/1969 | Bolhofer et al. | |
| 4,661,630 A | 4/1987 | Harigaya et al. | |
| 5,262,537 A | 11/1993 | Huang et al. | |
| 5,886,033 A | 3/1999 | Schwab et al. | |

FOREIGN PATENT DOCUMENTS

| | | |
|---|---|---|
| DE | 28 51 379 | 5/1979 |
| DE | 29 21 002 | 11/1979 |
| DE | 33 46 814 | 6/1984 |
| DE | 35 21 303 | 10/1985 |
| DE | 39 33 573 | 4/1991 |
| DE | 195 39 638 | 4/1997 |
| EP | 0 097 056 | 12/1983 |
| EP | 0 337 263 | 10/1989 |
| EP | 0 418 667 | 3/1991 |
| EP | 0 419 944 | 4/1991 |
| EP | 0 440 503 | 8/1991 |
| EP | 0 463 444 | 1/1992 |
| EP | 0 503 410 | 9/1992 |
| EP | 0 573 318 | 12/1993 |
| GB | 2 158 440 | 11/1985 |
| JP | 2-22650 | 1/1990 |
| WO | WO 98/57937 | 12/1998 |
| WO | WO 99/65867 | 12/1999 |
| WO | WO 01/21160 | 3/2001 |
| WO | WO 01/24785 | 4/2001 |
| WO | WO 02/38153 | 5/2002 |
| WO | WO 02/100851 | 12/2002 |
| WO | WO 03/006424 | 1/2003 |
| WO | WO 03/006425 | 1/2003 |
| WO | WO 03/006443 | 1/2003 |

OTHER PUBLICATIONS

Maruyama et al, J. Org. Chem, 1985, 50, 4742-4749.*
E. Kita, et al. Polish Journal of Chemistry, vol. 53, No. 6, pp. 1211-1219, "Protolytic Equilibriums of 4-Pyridoxyl-4, 5, 6, 7-Tetrahydropyrido-[3,4-C] Imidazole and its Derivatives", 1979 (submitting Chemical Abstracts only, An 1979; 592609).
F. Thorstensson, et al., Journal of Medicinal Chemistry, vol. 46, No. 7, XP-002274167, pp. 1165-1179, "Synthesis of Novel Thrombin Inhibitors. Use of Ring-Closing Metathesis Reactions for Synthesis of P2 Cyclopentene- and Cyclohexenedicarboxylic Acid Derivatives", 2003.

(Continued)

*Primary Examiner*—Shailendra Kumar
(74) *Attorney, Agent, or Firm*—Oblon, Spivak, McClelland, Maier & Neustadt, P.C.

(57) ABSTRACT

The present invention relates to compounds of the general formula (I) and salt and physiologically functional derivatives thereof,

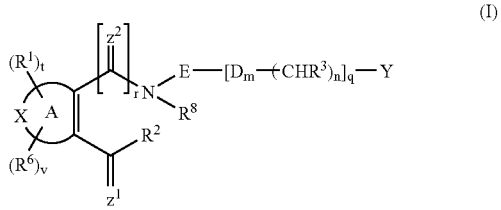

wherein A is a non-aromatic ring system containing 4 to 8 carbon atoms, wherein the ring system comprises at least one double bond and wherein one or more of the carbon atoms in the ring can be replaced by a group X, wherein X is selected from the group consisting of S, O, N, $NR^4$, SO, CO or $SO_2$;

D is O, S, $SO_2$, $NR^4$ or $CH_2$;

$Z^1$ and $Z^2$ are independent from each other O, S, or $NR^5$;

$R^2$ is H, $OR^6$, or $NHR^7$;

E is an alkyl or cycloalkyl group or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system for the use as a medicament.

23 Claims, No Drawings

OTHER PUBLICATIONS

S.-F. Chen, et al., Biochemical Pharmacology, vol. 40, No. 4, XP-000900094, pp. 709-714, "Structure-Activity Relationship of Quinoline Carboxylic Acids. A New Class of Inhibitors of Dihydroorotate Dehydrogenase", 1990.

J. V. De Julian-Ortiz, et al., Journal of Medicinal Chemistry, vol. 42, XP-002199074, pp. 3308-3314, "Virtual Combinatorial Syntheses and Computational Screening of New Potential Anti-Herpes Compounds", 1999.

Takeda Chemical Industries, et al., Chemical Abstracts+Indexes, vol. 94, No. 25, XP-002199076, 1 page, "Tetrahydrophthalamide Derivatives", Jun. 22, 1981.

Matsui, et al., Chemical Abstracts+Indexes, vol. 84, No. 5, XP-002199075, 1 page, "N-Substituted-Δ'-Cyclopentene-1, 2-Dicarboxylic Acid Monoamides as Herbicides", Feb. 2, 1976.

E. Campaigne, et al., J. Med. Chem., vol. 12, No. 2, XP-002278920, pp. 339-342, "Synthesis of Some Ureidodihydrofurans and Related Pyrimidones as Potential Antimalarials", 1969.

T. Trnovec, et al., Die Pharmazie, vol. 40, No. 6, XP-002275746, pp. 410-411, "Pharmacokinetics of Ethimizol in Man", Jun. 1985.

W. Küster, et al., Berichte Der Deutschen Chemischen Gesellschaft, vol. 57, No. 3, XP-002275747, pp. 409-413, "Über die Bildung von Pyrrol-Derivaten aus Amined von Beta-Diketonsäure-Estern.", Mar. 12, 1924.

N. Yasuda, Journal of Heterocyclic Chemistry, vol. 22, XP-002275748, pp. 413-416, "Synthesis of Novel Imidazole-4, 5-Dicarboxylic Acid Derivatives", 1985.

A. J. Carpenter, et al., Journal of Organic Chenistry, vol. 50, No. 22, XP-002275749, pp. 4362-4368, "The Scope and Limitations of Carboxamide-Induced β-Directed Metalation of 2-Substituted Furan, Thiophene, and 1-Methylpyrrole Derivatives. Application of the Method to Syntheses of 2, 3-Disubstituted Thiophenes and Furans", Nov. 1, 1985.

U.S. Appl. No. 10/736,711, filed Dec. 17, 2003, Leban et al.
U.S. Appl. No. 10/736,742, filed Dec. 17, 2003, Leban et al.
U.S. Appl. No. 10/736,739, filed Dec. 17, 2003, Leban et al.

* cited by examiner

COMPOUNDS AS ANTI-INFLAMMATORY, IMMUNOMODULATORY AND ANTI-PROLIFERATORY AGENTS

This application claims benefit of 60/435,258 filed Dec. 23, 2002.

DESCRIPTION

The present invention relates to novel compounds that can be used as antiinflammatory, immunomodulatory and anti-proliferatory agents. In particular the invention refers to new compounds which inhibit dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH).

Rheumatoid arthritis (RA) is a disease which is quite common especially among elder people. Its treatment with usual medications as for example non-steroid anti-inflammatory agents is not satisfactory. In view of the increasing ageing of the population, especially in the developed Western countries or in Japan the development of new medications for the treatment of RA is urgently required.

WO 99/38846 and EP 0 646 578 disclose compounds which are reported to be useful for treatment of RA.

A medicament against rheumatoid arthritis with a new mechanism of action, leflunomide, was recently put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis.

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immuno response, the lymphocytes, use exclusively the synthesis of pyrimidines for their growth and react particularly sensitively to DHODH inhibition. Substances that inhibit the growth of lymphocytes are important medicaments for the treatment of auto-immuno diseases.

The DHODH inhibiting leflunomide (ARAVA) is the first medicament of this class of compounds (leflunomides) for the treatment of rheumatoid arthritis. WO 99/45926 is a further reference that discloses compounds which act as inhibitors of DHODH.

WO 01/85685 discloses heterocylic derivatives such as thiadiazolidindiones for the treatment of a disease in which GSK-3 is involved, including Alzheimer's disease or the non-dependent insulin diabetes mellitus, or hyperprofilerative disease such as cancer, arterosclerosis or restenosis.

N-phenyltetrahydroisoindolediones and N-phenyltetrahydropyridazinediones (U.S. Pat. No. 5,719,104), 6-azolylcumarins (DE 3810706), arylheterocycles (EP 796845) and N-(heterocyclylphenyl) pyrroloimidazolsulfonamides (WO, 97/15576) are described as herbicides.

In J. Org. Chem. 1985, 50 (14), 2450–2456, pyrrolo[3,4-d]imidazole ring systems are described to have fluorescence properties.

In EP 463444, WO 98/57937, EP 150034, Nucleosides & Nucleotides 1997, 16 (10 & 11), 2025–2033; Egyptian Journal of Pharmaceutical Sciences 1991, 32 (1–2), 331–339, Journal für Praktische Chemie 1991, 333 (4), 619424, Archives of Pharmacal Research 1990, 13 (4), 338–341, Sulfur Letters 1988, 7 (4), 127–136, Synthesis 1988, 6 449–452, Sulfur Letters 1987, 7 (19), 19–24, Archiv der Pharmazie 1987, 320 (12), 1281–1283, Natl. Def., Med. Cent. 1983, 35 (1), 57–64 and Sch. Pharm. Sci. 1977, 97 (4), 410–415 a number of five membered aromatic ring systems fused to substituted maleimide are described.

It is an object of the present invention to provide alternative effective agent which can be used for the treatment of diseases which require the inhibition of DHODH.

Accordingly, a novel class of compounds with an inhibitory effect on DHODH, in particular human DHODH, was found.

The present invention is therefore directed to compounds of the general formula (I)

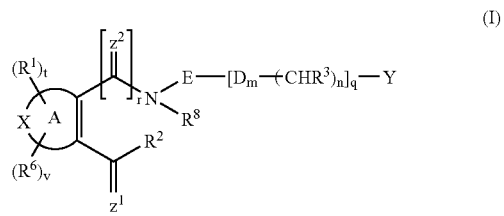

wherein

A is a non-aromatic ring system containing 4 to 8 carbon atoms, wherein the ring system comprises at least one double bond and wherein one or more of the carbon atoms in the ring can be replaced by a group X, wherein X is selected from the group consisting of S, O, N, $NR^4$, SO, CO or $SO_2$;

D is O, S, $SO_2$, $NR^4$ or $CH_2$;

$Z^1$ and $Z^2$ are independent from each other O, S, or $NR^5$;

$R^1$ is independently $-CO_2R''$, $-SO_3H$, $-CONR^*R''$, $-CR''O$, $-SO_2-NR^*R''$, $-NO_2$, $-SO_2-R''$, $-SO-R^*$, $-CN$, alkoxy, $-OH$, $-SH$, alkylthio, $-NR''-CO_2-R'$, $-NR''-CO-R^*$, $-NR''-SO_2R'$, $-O-CO-R^*$, $-O-CO_2-R^*$, $-O-CO-NR^*R''$; cycloalkyl, alkylamino, hydroxyalkylamino, aryl, or heteroaryl;

$R^9$ is independently H, halogen, haloalkyl, haloalkyloxy or alkyl;

R* is independently H: alkyl, cycloalkyl, aminoalkyl, alkoxy, $-OH$, $-SH$, alkylthio, hydroxyalkyl, haloalkyl, haloalkyloxy, aryl or heteroaryl;

R'' is independently hydrogen, haloalkyl, hydroxyalkyl, alkyl cycloalkyl, aryl, heteroaryl or aminoalkyl;

$R^2$ is H, $OR^6$, or $NHR^7$;

$R^3$ is H, alkyl, cycloalkyl, aryl, arylalkyl, alkoxy, O-aryl; O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;

$R^4$ is H, alkyl, cycloalkyl, aryl, or heteroaryl;

$R^5$ is H, OH, alkoxy, O-aryl, alkyl, or aryl;

$R^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;

$R^7$ is H, alkyl, aryl, alkoxy, O-aryl, cycloalkyl, or O-cycloalkyl;

$R^8$ is hydrogen or alkyl;

E is an alkyl or cycloalkyl group which is substituted by $[D_m\text{-}(CHR_3)_n]_q$ or a monocyclic or polycyclic substituted or unsubstituted ring system which may contain one or more groups X and which contains at least one aromatic ring;

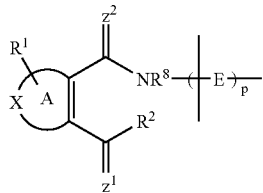

m is 0 or 1;
n is 0 or 1;
p is 0 or 1;
r is 0 or 1;
q is 0 or 1;
t is 1 to 3; and
v is 0 to 3;

The present invention is also directed to compounds of the general formula (Ia)

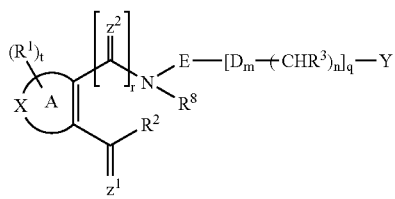

(Ia)

wherein
A is a non-aromatic ring system containing 4, 5, 6, 7 or 8 carbon atoms, wherein the ring system comprises at least one double bond and wherein one or more of the carbon atoms in the ring can be replaced by a group X, wherein X is selected from the group consisting of S, O, N, $NR^4$, SO, CO or $SO_2$;
D is O, S, $SO_2$, $NR^4$, or $CH_2$;
$Z^1$ and $Z^2$ are independent from each other O, S, or $NR^5$;
$R^1$ is independently H, halogen, haloalkyl, haloalkyloxy —$CO_2R"$, —$SO_3H$, —OH —$CONR*R"$, —$CR"O$, —$SO_2$—$NR*R"$, —$NO_2$, —$SO_2$—$R"$, —$SO$—$R*$, —CN, alkoxy, alkylthio, aryl, —$NR"$—$CO_2$—$R'$, —$NR"$—$CO$—$R*$, —$NR"$—$SO_2$—$R'$, —O—CO—$R*$, —O—$CO_2$—$R*$, —O—CO—$NR*R"$; cycloalkyl, alkylamino, hydroxyalkylamino, —SH, heteroaryl, or alkyl;
R* is independently H, alkyl, cycloalkyl, aminoalkyl, alkoxy, —OH, —SH, alkylthio, hydroxyalkyl, haloalkyl, haloalkyloxy, aryl or heteroaryl;
R" is independently hydrogen, haloalkyl, hydroxyalkyl, alkyl, cycloalkyl, aryl, heteroaryl or aminoalkyl;
$R^2$ is NHOH or $R^2$ together with the nitrogen atom which is attached to $R^8$ form a 5 or 6 membered heterocyclic ring with the proviso that $R^2$ is —$[CH_2]_s$ and $R^8$ is absent;
$R^3$ is H, alkyl, cycloalkyl, aryl alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl or haloalkyl;
$R^4$ is H, alkyl, cycloalkyl, aryl or heteroaryl;

$R^5$ is H, OH, alkoxy, O-aryl, alkyl or aryl; $R^8$ is hydrogen, or alkyl;
E is an alkyl or cycloalkyl group which is substituted by $[D_m$-$(CHR_3)_n]_qY$ or a monocyclic or polycyclic substituted or unsubstituted ring system which may contain one or more groups X and which contains at least one aromatic ring;
Y is hydrogen halogen, haloalkyl, haloalkyloxy, alkyl, cycloalkyl, a monocyclic or polycyclic substituted or unsubstituted ring system which may contain one or more groups X and which contains at least one aromatic ring or

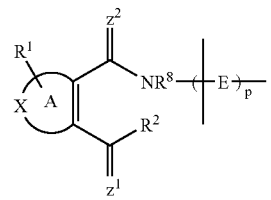

m is 0 or 1;
n is 0 or 1;
p is 0 or 1;
r is 0 or 1;
q is 0 or 1;
s is 0 to 2; and
t is 0 to 3;
with the proviso that the following compounds are excluded:
compounds wherein ring A is an unsubstituted carbocycle containing six carbon atoms and one double bond between the $CZ^1$ and $CZ^2$-substituents, $Z^1$=$Z^2$=O, and s is 0; 1,3,5-Tribenzyl-2,4,6-trioxopyrrolo[3,4-d]imidazole, 1,3-Dibenzyl-5-(4-methoxy-benzyl)-2,4,6-trioxopyrrolo[3,4-d]imidazole, 1,3-Bis-(4-methoxybenzyl)-5-benzyl-2,4,6-trioxopyrrolo[3,4-d]imidazole, and 1,3-Tris-(4-methoxybenzyl)-2,4,6-trioxo-pyrrolo[3,4-d]imidazole.

The present invention is also directed to compounds of the general formula (III)

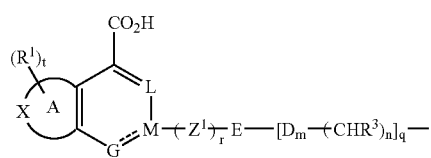

(III)

wherein
the bond between G and M is a single or double bond;
A is a non-aromatic ring system containing 4, 5, 6, 7 or 8 carbon atoms, wherein the ring system comprises at least one double bond and wherein one or more of the carbon atoms in the ring can be replace by a group X, wherein X is selected from the group consisting of S, O, N, $NR^4$, SO, CO or $SO_2$;
D is O, S, $SO_2$, $NR^4$, or $CH_2$;
G is O, S, $SO_2$, CO, N, $NR^4$, $CR^1$ or $CHR^1$;
L is N or $CR^1$;
M is N or $CR^5$;
$Z^1$ is O, S, or $NR^5$; $NR^4CONR^4$, $CONR^4$, or CO;

$R^1$ is independently H, halogen, haloalkyl, haloalkyloxy —$CO_2R''$, —$SO_3H$, —OH, —$CONR*R''$, —$CR''O$, —$SO_2$—$NR*R''$, —$NO_2$, —$SO_2$—$R''$, —$SO$—$R*$, —CN, alkoxy, alkylthio, aryl, —$NR''$—$CO_2$—$R'$, —$NR''CO$—$R*$, —$NR''$—$SO_2$—$R'$, —O—CO—$R*$, O—$CO_2$—$R*$, —O—CO—$NR*R''$; cycloalkyl, alkylamino, hydroxyalkylamino, —SH, heteroaryl, or alkyl;

$R*$ is independently H, alkyl, cycloalkyl, aminoalkyl, alkoxy, —OH, —SH, alkylthio, hydroxyalkyl, haloalkyl, haloalkyloxy, aryl or heteroaryl;

$R''$ is independently hydrogen, haloalkyl, hydroxyalkyl, alkyl, cycloalkyl, aryl, heteroaryl or aminoalkyl;

$R^3$ is H, alkyl, cycloalkyl, aryl, alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl, or haloalkyl;

$R^4$ is H, alkyl, cycloalkyl, aryl or heteroaryl;

$R^5$ is H, OH, alkoxy, O-aryl, alkyl or aryl;

$R^7$ is H, OH, alkyl, aryl, alkoxy, O-aryl, cycloalkyl, or O-cycloalkyl;

$R^8$ is hydrogen, or alkyl;

E is an alkyl or cycloalkyl group which is substituted by $[D_m\text{-}(CHR_3)_n]_qY$ or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

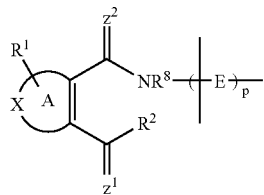

m is 0 or 1;
n is 0 or 1;
p is 0 or 1;
r is 0 or 1;
q is 0 or 1; and
t is 0 to 3;

The present invention is also directed to compounds of the general formula (IV)

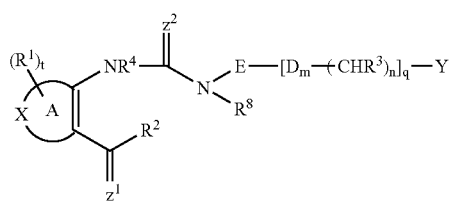

(IV)

wherein

A is a non-aromatic ring system containing 4, 5, 6, 7 or 8 carbon atoms, wherein the ring system comprises at least one double bond and wherein one or more of the carbon atoms in the ring can be replaced by a group X, wherein X is selected from the group consisting of S, O, N, $NR^4$, SO, CO or $SO_2$;

D is O, S, $SO_2$, $NR^4$, or $CH_2$;

$Z^1$ and $Z^2$ are independent from each other O, S, or $NR^5$, $R^1$ is independently H, halogen, haloalkyl, haloalkyloxy —$CO_2R''$, —$SO_3H$, —OH, —$CONR*R''$, —$CR''O$, —$SO_2$—$NR*R''$, —$NO_2$, —$SO_2$—$R''$, —$SO$—$R*$, —CN, alkoxy, alkylthio, aryl, —$NR''$—$CO_2$—$R'$, —$NR''$—CO—$R*$, —$NR''$—$SO_2$—$R'$, —O—CO—$R*$, —O—$CO_2$—$R*$, —O—CO—$NR*R''$; cycloalkyl, alkylamino, hydroxyalkylamino, heteroaryl, —SH, or alkyl;

$R^2$ is H or $OR^6$, $NHR^7$, $NR^7OR^7$ or $R^2$ togehter with the nitrogen atom which is attached to $R^8$ form a 6 membered heteroyclic ring with the proviso that $R^2$ is —$[CH_2]_8$ and $R^8$ is absent;

$R^3$ is H, alkyl, cycloalkyl, aryl, alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl, or haloalkyl;

$R^4$ is H, alkyl, cycloalkyl, aryl or heteroaryl;

$R^5$ is H, OH, alkoxy, O-aryl, alkyl or aryl;

$R^6$ is H, alkyl cycloalkyl aryl, arylalkyl, heteroaryl, alkylaryl alkoxyalkyl, acylmethyl, (acyloxy)alkyl, non-symmetrical (acyloxy)alkyldiester, or dialkylphosphate;

$R^7$ is H, OH, alkyl, aryl, alkoxy, O-aryl, cycloalkyl, or O-cycloalkyl;

$R^8$ is hydrogen, or alkyl;

E is an alkyl or cycloalkyl group which is substituted by $[D_m\text{-}(CHR_3)_n]_qY$ or a monocyclic or polycyclic substituted or unsubstituted ring system which may contain one or more groups X and which contains at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

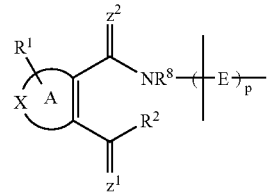

m is 0 or 1;
n is 0 or 1;
p is 0 or 1;
q is 0 or 1;
s is 0 to 2;
t is 0 to 3;

with the proviso that the following compounds are excluded: 5,5-Dimethyl-4-phenyl-2-(3-phenyl-ureido)-4,5-dihydro-furan-3-carboxylic acid methyl ester, 2[3-(4-Chlorophenyl-ureido)]-5,5-dimethyl-4-phenyl-4,5-dihydro-furan-3-carboxylic acid methyl ester, 2[3-(4-Methoxylphenyl-ureido)]-5,5-dimethyl-4-phenyl-4,5-dihydro-furan-3-carboxylic acid methyl ester, 2[3-(4-Methylphenyl-ureido)]-5,5-dimethyl-4-phenyl-4,5-dihydro-furan-3-caboxylic acid methyl ester, 2[3-(4-Nitrophenyl-ureido)]-5,5-dimethyl-4-phenyl-4,5- dihydro-furan-3-carboxylic acid methyl ester, 4-(4-Chlorophenyl)-5,5-dimethyl-2-(3-phenyl-ureido)-4,5-dihydro-furan-3-carboxylic acid methyl ester, 4-(4-Chlorophenyl)-2[3-(4-chlorophenyl-ureido)]-5,5-dimethyl-4,5-dihydro-furan-3-carboxylic acid methyl ester, 4-(4-Chlorophenyl)-2[3-(4-methoxyphenyl-ureido)]-5,5-dimethyl-4,5-dihydro-furan-3-carboxylic acid methyl ester, 4-(4-Chlorophenyl)-2[3-(4-methylphenyl-ureido)]-5,5-dimethyl-4,5-dihydro-furan-3-carboxylic acid methyl ester, or 4-(4-Chlorophenyl)-2 [3-(4-nitrophenyl-ureido)]-5,5-dimethyl-4,5-dihydro-furan-3-caboxylic acid methyl ester, an alkyl group, if not stated otherwise, denotes a linear or branched $C_1$–$C_6$-alkyl, preferably a linear or branched chain of one to five carbon atoms, a linear or branched $C_1$–$C_6$-alkenyl or a linear or branched $C_1$–$C_6$ alkinyl group, which can optionally be substituted by one or more substituents R', preferably by halogen;

the $C_1$–$C_6$-alkyl, $C_1$–$C_6$-alkenyl and $C_1$–$C_6$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($C_3$)—CH=$C_2$, —CH=CH—C($CH_3$)=$CH_2$, —CH=C($CH_3$)$_2$, C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$C≡C—$CH_3$, —$CH_2$C≡C—$C_3H_7$, —$C_2H_4$C≡$C_2H_5$;

R' is independently H, —$CO_2$R", —CONHR", —CR"O, —$SO_2$NR", —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl arylalkyl or heteroaryl;

R" is independently hydrogen, haloalkyl, hydroxyalkyl, alkyl, cycloalkyl, aryl, heteroaryl or aminoalkyl;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$–$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above, an haloalkyl group denotes an alkyl group which is substituted by one to five halogen atoms, the alkyl group being as defined above; the haloalkyl group is preferably a —C($R^{10}$)$_3$, —$CR^{10}$($R^{10'}$)$_2$, —$CR^{10}$($R^{10'}$)$R^{10"}$, —$C_2$($R^{10}$)$_5$, —$CH_2$—C($R^{10}$)$_3$, —$CH_2$—$CR^{10}$($R^{10'}$)$_2$, —$CH_2$—$CR^{10}$($R^{10'}$)$R^{10"}$, —$C_3$($R^{10}$)$_7$ or —$C_2H_4$—C($R^{10}$)$_3$, wherein $R^{10}$, $R^{10'}$, $R^{10"}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —$OCR^{10}$($R^{10'}$)$_2$, —$OCR^{10}$($R^{10'}$)$R^{10"}$, —$OC_2$($R^{10}$)$_5$, —$OCH_2$—C($R^{10}$)$_3$, —$OCH_2$—$CR^{10}$($R^{10'}$)$_2$, —$OCH_2$—$CR^{10}$($R^{10'}$)$R^{10"}$, —$OC_3$($R^{10}$)$_7$ or —$OC_2H_4$—C($R^{10}$)$_3$, wherein $R^{10}$, $R^{10'}$, $R^{10"}$ represent F, Cl, Br or I, preferably F;

a hydroxyalkylamino group denotes an (HO-alkyl)$_2$-N— group or HO-alkyl-NH— group, the alkyl group being as defined above;

an alkyl no group denotes an HN-alkyl or N-dialkyl group, the alkyl group being as defined above;

a halogen group is chlorine, bromine, fluorine or iodine, fluorine being preferred;

an aryl group preferably denotes an aromatic group having five to fifteen carbon atoms, which can optionally be substituted by one or more substituents R', where R' is as defined above; the aryl group is preferably a phenyl group, —$CH_2$Ph, —$C_2H_4$Ph, —CH=CH—Ph, —C≡C—Ph, -o-$C_6H_4$—R', -m-$C_6H_4$—R', -p-$C_6H_4$—R', -o-$CH_2$—$C_6H_4$—R', -m-$CH_2$—$C_6H_4$—R', -p-$CH_2$—$C_6H_4$—R';

a heteroaryl group denotes a 5- or 6-membered heterocyclic group which contains at least one heteroatom like O, N, S. This heterocyclic group ran be fused to another rig. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo-[b]-furanyl, benzo[b]thiophenyl, benzimidazolyl benzothiazolyl, quinazolinyl, quinoxazolinyl; or preferably quinolinyl, tetrahydroquinolinyl, isoquinolinyl, tetrahydroisoqulnolinyl group. This heterocyclic group can optionally be substituted by one or more substituents R', where R' is as defined above.

The meaning of E includes optional by one or more substituents R' substituted alkyl groups, wherein alkyl is defined as above or as a cycloalkyl group optionally substituted by one or more substituents R' such as cyclopropyl, cyclobutyl, cyclopentyl, cyclohexyl, cycloheptyl, cyclooctyl or carbocyclic aromatic groups such as phenyl, 1-naphthyl, 2-naphthyl, anthracenyl, in particular 1-anthracenyl and 2-anthracenyl, and heterocyclic aromatic groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl. E includes also fused polycyclic aromatic ring systems such as 9H-thioxanthene-10,10-dioxide in which a carbocyclic aromatic ring or heteroaryl ring is fused to one or more other heteroaryl ring.

The invention also provides a pharmaceutical composition comprising a compound of formula (I) or of formula (III), or of formula (Ia), or of formula (IV) including the compounds excluded by the disclaimers, in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

In another aspect, the present invention also provides a method for the treatment or prophylaxis of a condition where there is an advantage in inhibiting dihydroorotate dehydrogenase (DHODH) which comprises the administration of an effective amount of a compound of formula (I), (Ia), (III), or of formula (IV) and physiologically acceptable salts or physiologically functional derivatives thereof.

The invention is also directed to the use of compounds of the formula (I), (Ia), (III) or of formula (IV) and of their pharmacologically tolerable salts or physiologically functional derivatives for the production of a medicament for the prevention and treatment of diseases, where inhibition of the pyrimidine biosynthesis is of benefit.

In addition, the present invention provides methods for preparing the compounds of the invention such as compounds of formula (I), of formula (Ia), of formula (III), or of formula (IV).

The compounds of formula (I), of formula (Ia), or of formula. (III) may be obtained via various methods. In preferred embodiments of the methods of the invention the following methods of synthesis are used.

For the synthesis of dicarboxylic acids substituted in or on the ring system two methods were used.

Method 1:
The synthesis of dicarboxylic acid dimethylester is described in WO 02/07655. This dicarboxylic acid dimethyl ester can be substituted on the ring system as desciBed by T. Harrison et.al., Tetrahedron Vol. 45, No.16, 1989, 5247–5262. This dicarboxylic acid dimethyl ester can then be converted into the corresponding acid anhydride.

Method 2: Dicarboxylic acids substituted in or on the ring system can also be synthesized in general via the cyanhydrine synthesis [Shwu-Jiüan Lee et al., Bull. Inst. Chem. Academia Sinica Number 40, (1993), 1–10 or B. R. Baker at al., J. Org. Chem. 13, 1948, 123–133; and B. R. Baker at al., J. Org. Chem. 12, 1947, 328–332; L. A. Paquette et. al., J. Am. Chem. Soc. 97, (1975), 6124–6134]. This dicarboxylic acid can then be converted into the corresponding acid anhydride.

These anhydrides may then be reacted with the corresponding amines to the desired amides of formula (I), of formula (Ia), or of formula (IV). This reaction steps are analog to the reaction steps described in WO 02/07655.

The compounds of formula (I), or of formula (Ia), in each case [r=0] can be synthesized analog to the four methods described in WO 02/07655.

The invention also provides methods for preparing compounds of formula (Ia) wherein $R^2$ together with the nitrogen atom which is attached to $R^8$ form a 6 membered heterocylic ring system.

The respective substituted aniline of formula (Ia) prepared in analogy to WO 02/07655 was deprotonated with sodium hydride in tetrahydrofuran and alkylated with 2-bromomethyl-[1,3]dioxolane. Starting from 2-(carbethoxy)cyclopentanone, 2-(aminiocarbonyl)-2-cyclopentene-1-ones were synthesized by amidation using the corresponding N-alkyl aniline and 4-dimethylaminopyridine, followed by oxidation with lead tetraacetate in the presence of catalytic amounts of copper(II) acetate (A. G. Schulz et al., Tetrahedron Lett. 34, 1993, 3021–3024). Deacetalization at the aniline side chain set free an aldehydic group, which was used for a Stetter reaction by reversion of polarity with thiazolium salts and subsequent 1,4-addition (H. Stetter, Angew. Chem. 88, 1976, 695–704).

In addition, the present invention provides methods for preparing the desired hydroxamic acides of formula (Ia), or of formula (IV).

One method for the synthesis of compounds of formula (Ia), or of formula (IV) comprises the conversion of an acid to the corresponding acid chloride and reacting the acid chloride with hydroxylamine (Watanabe et al., 1989, J. Org. Chem., 54, 17, 4088–4097; Shishido et al., 1992, J. Org. Chem., 57, 10, 2876–2883).

Other methods for the preparation of compounds of formula (Ia), or of formula (IV) are described by Woo et al., 2002, J. Med. Chem. 45, 2877–2885; Knorr et al., 1989, Tetrahedron Lett., 30, 1927–1930, Carpino, 1993, J. Am. Chem. Soc., 115, 4397–4398 and Albericio et.al., 1998, J. Org. Chem., 63, 9678–9683.

Another method for the preparation of compounds of formula (Ia), or of formula (IV) is the reaction of the corresponding ester with hydroxylamine as described by Stowell et al., 1995, J. Med. Chem., 38, 8, 1411–1413.

The synthesis of amides of formula (Ia), or of formula (IV) is described by J. Zabicky in "The Chemistry of Amides", in the serial of S. Patai (ed.), "The Chemistry of Functional Groups", John Wiley & Sons, 1975, p. 74–131. Methods for preparing thioamides are described in Houben-Weyl, J. Falbe (ed.), G. Thieme Verlag, vol. E5, p. 1219–59. Methods for preparing sulfamides are described by Caldwell et al., *J. Am. Chem. Soc.* 1944, 66, 1479–82, or by Flynn et al., *Med. Chem. Res.*, 1998, 8, 219–43 and Dziadulewicz et al., *Bioorg. Med. Chem. Lett.* 2001, 11, 5, 705–10.

One possible method for preparing compounds of the present invention of formula (III) is analogue WO 99/38846. The synthesis is described for compounds of formula (III) wherein G, L are carbon atoms and M is nitrogen (page 14), or M is a carbon atom and G and L are nitrogen atoms (page 16) or L and M are carbon atoms and G is nitrogen, or G,M and L are carbon atoms (page 19).

Methods for preparing different ureas of formula (IV) are described for example in WO 99/38846, *Organic Synthesis* on *Solid Phase*, Ed. F. Z. Dörwald, p. 331ff, Wiley-VCH, Weinheim 1999 or in Houben-Weyl, vol. E4, *Kohlensäure-Derivate [Caboxylic acid derivatives]* Publisher Hagemann, Georg Thieme Verlag, Stuttgart, 1983 and asymmetric ureas are described in R. A. Batey, *Tetrahedron Letters* 1998, 39, 6267–70. Thioureas for example are described in *Bull. Soc. Chim., Belg Synth*. 1978, 87, 229–38, in *Org. Synth*. 1984, 62, 158–64 or *Chem. Rev*. 1961, 61, 45–86 J. *Comb. Chem*., 2000, 2, 75–79 and in Houben-Weyl, Vol. E4, *Kohlensäure-Derivate [Carbonic acid derivatives]*, Editor Hagemann, Georg Thieme Verlag, Stuttgart, 1983, 484–505.

In the compounds of formula (I), of formula (Ia), of formula (III), or of formula (IV) the non-aromatic ring system. A contains 4, 5, 6, 7 or 8, preferably 5 carbon atoms. The ring system. A comprises at least one double bond which is located between carbon atoms carrying the substituents —$CZ^1$- and —$CZ^2$. In preferred embodiments, the compounds of the present invention contain only this double bond. In case of two or more double bonds, these double bonds are not-conjugated. One or more of the carbon atoms in the ring system A can be replaced by a group X, wherein X is selected from the group consisting of S, O, N, $NR^4$, SO, CO or $SO_2$. In one preferred embodiment, one carbon atom is replaced by a group X=S, X=CO, or X=O. In a more preferred embodiment, none of the carbon atoms is replaced by a group X.

In another preferred embodiment, in the compounds of formula (I), of formula (Ia), of formula (III), or of formula (IV), A is 1-cyclopenten-1,2-diyl, 2,5-dihydro-thiophene-3, 4-diyl, 2,5-dihydro-furan-3,4-diyl, 2,5-dihydro-1H-pyrrole-3,4-diyl, 2,5-dihydro-1-methyl-pyrrole-3,4-diyl, 2,5-dihydro-1-methyl-pyrrole-3,4-diyl, 2,5-dihydro-1-acetyl-pyrrole-3,4-diyl, 2,5-dihydro-1-methyl-sulfonyl-pyrrole-3,4-diyl.

In another preferred embodiment, in the compounds of formula (I), of formula (Ia), of formula (III), or of formula (IV), A is 1-cyclobuten-1,2-diyl, 1-cyclohexen-1,2-diyl, 1-cyclohepten-1,2-diyl or 1-cycloocten-1,2-diyl.

In another preferred embodiment, in the compounds of formula (I), or of formula (Ia), 3 position on the 1-cyclobuten-1,2-diyl ring system.

In another preferred embodiment, in the compounds of formula (I), or of formula (Ia), 5 position on the 1-cyclobuten-1,2-diyl ring system In the compounds of formula (I), of formula (Ia), or of formula (III) $R^1$ is preferably OH, $OCH_3$, SH, $CO_2H$ or $SO_3H$ or tetrazole.

In the compounds of formula (I) $R^9$ is preferably H.

In the compounds of formula (I) $R^2$ is H, $OR^6$, preferably OH or $OR^6$.

In the compounds of formula (Ia) $R^2$ is preferably NHOH.

In the compounds of formula (IV), $R^2$ is preferably OH, $NH_2$, NHOH, $NHR^7$, $NR^7OR^7$ or $OR^6$.

In preferred embodiment, in the compounds of formula (I), or of formula (IV), $R^6$ is benzoyloxymethyl, isobutyryloxymethyl-1,4-amino-butyryloxymethyl, butyryloxymethyl, 1-(butyryloxy)ethyl, 1-(butyryloxy)-2,2-dimethylpropyl, 1-diethyl-phosphonooxyethyl, 2-(2-methoxyethoxy)-acetyloxymethyl, p-aminobenzoyl-methyl, nicotinyloxymethyl, pivalyloxymethyl, glutaryloxymethyl, [2-(2-methoxy-ethoxy)ethoxy]-acetyloxymethyl, 2-(morpholine-4-yl)-ethyl, 1-diethyl-phosphono-oxymethyl.

In the compounds of formula (I), of formula (Ia), of formula (II), of formula (III), of formula (IV), or of formula (V) $R^3$ is is H, alkyl, cycloalkyl, aryl, alkoxy, O-aryl, O-cycloalkyl, halogen, aminoalkyl, alkylamino, hydroxy-lamino, haloalkyl, hydroxylalkyl, haloalkyloxy, heteroaryl, alkylthio, S-aryl; S-cycloalkyl, arylalkyl, preferably H.

In the compounds of formula (I), of formula (Ia), of formula (III), or of formula (IV) $R^4$ is H, alkyl, cycloalkyl, aryl or heteroaryl, preferably H.

In formula (I), in formula (Ia), or in formula (IV) $R^8$ is H or alkyl, preferably H or methyl.

In formula (I), in formula (Ia), or in formula (IV) $Z^1$ and $Z^2$ are independent from each other O, S, or $NR^5$, preferably both are O.

In formula (III) $Z^1$ is O, S, or $NR^5$, preferably it is O.

In formula (I), of formula (Ia), of formula (III), or of formula (IV) Y is hydrogen, halogen, alkyl substituted or unsubstituted cycloalkyl, substituted or unsubstituted E, substituted or unsubstituted O-E, substituted or unsubstituted O-alkylaryl, substituted or unsubstituted O-arylalkyl; in case of said substitution, substitution of one or more hydrogen atoms of the alkyl-, cycloalkyl-, or aryl-groups by halogens are preferred. Y can also be

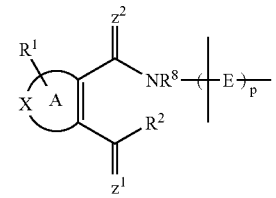

wherein A, X, $R^1$, $R^2$, $R^8$, $Z^1$, $Z^2$ and p have the meaning as define above. Preferably Y is E and more preferably Y is an optionally substituted phenyl.

In formula (I), of formula (Ia), of formula (III), or of formula (IV) E is an alkyl or cycloalkyl group which is optionally substituted by one or more substituents R', or E is a monocyclic or polycyclic substituted or unsubstituted ring system which contains at least one aromatic ring and which may also contain one or more groups X selected from S, O, N, $NR^4$, SO or $SO_2$. In preferred embodiments, E is a monocyclic aromatic ring or an aromatic bicyclic or tricyclic ring system, or cycloalkyl. In case of substitutions of carbon atoms in the ring system, preferably one, two or three carbon atoms are replaced by a group X as defined above.

In formula (I), of formula (Ia), of formula (III), or of formula (E is preferably an optionally by one or more substituents R' substituted phenyl, 1-naphtyl, 2-naphthyl, 1-anthracyl and 2-anthracyl.

In a preferred embodiment of the present invention in compounds of formula (I), of formula (Ia), of formula (III), or of formula (IV) E is an optionally by one or more substituents R' substituted phenyl, or an optionally by one or more substituents R' substituted cycloalkyl.

In formula (I), of formula (Ia), of formula (III), or of formula (IV) preferred substituents R' are nitro, halogen, alkoxy, haloalkyl, haloalkyloxy, heteroaryl, alkyl or aryl, more preferably R' is Br, F, Cl, $CF_3$, $OCF_3$, ethoxy or methoxy.

In formula (I), of formula (Ia), of formula (III), or of formula (IV) preferred heteroaryl groups are imidazoyl, thienyl, furanyl, pyridyl, pyrimidyl, pyranyl, pyrazolyl, pyrazinyl, thiazolyl, 1H-tetrazol-2-yl, 1H-tetrazol-3-yl, or oxazolyl.

In formula (I) t is preferably 1 or 2.

In formula (Ia), in formula (III), or in formula (IV) t is preferably 0, 1 or 2.

In formula (I) v is preferably 0 or 1.
In formula (Ia), or in formula (IV) s is preferably 0 or 1
In formula (III) r is preferably 0.
In formula (III) L is preferably a carbon or nitrogen atom.
In formula (III) M is preferably a nitrogen atom or a carbon atom.
In formula (III) G is preferably a carbon, CO or a nitrogen atom.

In particular preferred embodiment of the invention, in compounds of formula (III) L, M and G are carbon atoms, r=0, q=0, t=1, E is phenylene which is either unsubstituted or substituted with F, Cl and/or $CF_3$ or $OCF_3$, and Y is phenylene which is either unsubstituted or substituted with F, Cl and/or $CF_3$ or $OCF_3$, and A is a five membered ring.

In particular preferred embodiment of the invention, in compounds of formula (III) L, M and G are carbon atoms, r=0, t=1, E is phenylene which is either unsubstituted or substituted with F, Cl and/or $CF_3$ or $OCF_3$, and Y is H or F, ad A is a five membered ring.

In another particularly preferred embodiment of the invention, in compounds of formula (III) L is a carbon atom, and M is a nitrogen atom, G=CO, r=0, q=0, t=1, E is phenylene which is either unsubstituted or substituted with F, Cl and/or $CF_3$ or $OCF_3$, and Y is phenylene which is either unsubstituted or substituted with F, Cl and/or $CF_3$ or $OCF_3$, and A is a five membered ring, and the dotted line is absent.

In another particularly preferred embodiment of the invention, in compounds of formula (III) L is a carbon atom, and M is a nitrogen atom, G=CO, r=0, t×1, E is phenylene which is either unsubstituted or substituted with F, Cl and/or $CF_3$ or $OCF_3$, and Y is H or F, and A is a five membered ring, and the dotted line is absent.

In other particularly preferred embodiment of the invention, in compounds of formula (III) L and M are nitrogen atoms, G=CO, r=0, q=0, t=1, E is phenylene which is either unsubstituted or substituted with F, Cl and/or $CF_3$ or $OCF_3$, and Y is phenylene which is either unsubstituted or substituted with F, Cl and/or $CF_3$ or $OCF_3$, and A is a five membered ring, and the dotted line is absent.

In other particularly preferred embodiment of the invention, in compounds of formula (H) L and M are nitrogen atoms, G=CO, r=0, t=1, E is phenylene which is either unsubstituted or substituted with F, Cl and/or $CF_3$ or $OCF_3$, and Y is H or F, and A is a five membered ring, and the dotted line is absent.

In further particularly preferred embodiment, in compounds of formula (III) L and M are carbon atoms, and G is nitrogen atom $Z^1$=O (thus r=1), q=0, t=1, E is phenylene which is either unsubstituted or substituted with F, Cl and/or $CF_3$ or $OCF_3$, and Y is phenylene which is either unsubstituted or substituted with F, Cl and/or $CF_3$ or $OCF_3$, and A is a five membered ring, and the dotted line is a bond.

In further particularly preferred embodiment, in compounds of formula (III) L and M are carbon atoms, and G is nitrogen atom, $Z^1$=O (thus r=1), t=1, E is phenylene which is either unsubstituted or substituted with F, Cl and/or $CF_3$ or $OCF_3$, and Y is H or F, and A is a five membered ring, and the dotted line is a bond.

In further particularly preferred embodiment, in compounds of formula (III), M is a carbon atom, L and G are nitrogen atoms, E is phenylene which is either unsubstituted or substituted with F, Cl and/or $CF_3$ or $OCF_3$, and Y is phenylene which is either unsubstituted or substituted with F, Cl and/or $CF_3$ or $OCF_3$, and A is a five membered ring, and the doted line is a bond.

In further particularly preferred embodiment, in compounds of formula (III), M is a carbon atom, L and G are nitrogen atoms, E is phenylene which is either unsubstituted or substituted with F, Cl and/or $CF_3$ or $OCF_3$, and Y is H or F, and A is a five membered ring, and the dotted line is a bond.

In the compounds of formula (I), of formula (Ia), of formula (III), or of formula (IV) D is O, S, $SO_2$, $NR^4$, or $CH_2$. D is preferably S or, more preferably O, when m=1.

In other preferred embodiment, in the compounds of formula (I), of formula (Ia), of formula (III), or of formula (IV) m and q are zero and Y is hydrogen, halogen, haloalkyl, haloalkyloxy, alkyl, cycloalkyl or E, preferably F, $CF_3$, $OCF_3$, an optionally by one or more substituents R' substituted phenyl or more preferably an optionally by one or more F, Cl, methoxy, ethoxy, $CF_3$, or $OCF_3$ substituted phenyl.

In particular preferred embodiment of the invention, in compounds of formula (I), of formula (Ia), of formula (III), or of formula (IV), q=0, t=1, and A is a carbocyclic non-aromatic ring system, Y is H or F, or E is phenyl which is either unsubstituted or substituted with Cl, F and/or $CF_3$ or $OCF_3$.

In another particularly preferred embodiment of the invention, in compounds of formula (I) of formula (Ia), of formula (III), or of formula (IV) q=0, t=1, and A is a carbocyclic non-aromatic ring system, and E and Y are substituted or unsubstituted phenylene and phenyl, respectively.

In further particularly preferred embodiment, in compounds of formula (I) of formula (Ia), of formula (III), or of formula (IV), D=O (thus m=1), $R^3$ is H (thus n=1), q=1, t=1, and E is phenylene which is either unsubstituted or substituted with Cl, F and/or $CF_3$ or $OCF_3$, and Y is phenyl which is also either unsubstituted or substituted with Cl, F and/or $CF_3$, methoxy, ethoxy, or $OCF_3$, and A is a carbocyclic non-aromatic ring system.

In further particularly preferred embodiment, in compounds of formula (I) of formula (Ia), of formula (III), or of formula (IV) D=O (thus m=1), n=0, q=1, t=1, and E is phenylene which is either unsubstituted or substituted with Cl, F and/or $CF_3$ or $OCF_3$, and Y is phenyl which is also either unsubstituted or substituted with Cl, F and/or $CF_3$, methoxy, ethoxy, or $OCF_3$, and A is a carbocyclic non-aromatic ring system.

In further particularly preferred embodiment, in compounds of formula (I) of formula (Ia), of formula (III), or of formula (IV), DS (thus m=1), n=0, q=1, t=1, and E is phenylene which is either unsubstituted or substituted with Cl, F and/or $CF_3$ or $OCF_3$; and Y is phenyl which is also either unsubstituted or substituted with methoxy, ethoxy, Cl, F and/or $CF_3$ or $OCF_3$, and A is a carbocyclic non-aromatic ring system.

In particular preferred embodiment of the invention, in compounds of formula (I), of formula (Ia), of formula (III), or of formula (IV), q=0, t=1, and A is a non-aromatic ring system, wherein one carbon atom is replaced by O, or Y is H or F, and E is phenyl which is either unsubstituted or substituted with Cl, F and/or $CF_3$ or $OCF_3$.

In another particularly preferred embodiment of the invention, in compounds of formula (I), of formula (Ia), of formula (III), or of formula (IV), q=1, t=1, and A is a non aromatic ring system, wherein one carbon atom is replaced by O, or E and Y are substituted or unsubstituted phenylene and phenyl, respectively.

In further particularly preferred embodiment, in compounds of formula (I), of formula (Ia), of formula (III), or of formula (IV), D=O (thus m=1), $R^3$ is H (thus n=1), q=1, t=1, and E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and A is a non-aromatic ring system, wherein one carbon atom is replaced by O.

In further particularly preferred embodiment, in compounds of formula (I), of formula (Ia), of formula (III), or of formula (IV), D=O (thus m=1), n=0, q=1, t=1, and E is phenylene which is either unsubstituted or substituted with Cl, F and/or $CF_3$ or $OCF_3$, and Y is phenyl which is also either unsubstituted or substituted with Cl, F and/or $CF_3$ or $OCF_3$, and A is a non-aromatic ring system, wherein one carbon atom is replaced by O.

In further particularly preferred embodiment, in compounds of formula (I), of formula (Ia), of formula (III), or of formula (IV), D=S (thus m-1), n=0, q=1, t=1, and E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and A is a non-aromatic ring system, wherein one carbon atom is replaced by O.

In particular preferred embodiments of the invention, in compounds of formula (I), of formula (Ia), of formula (III), or of formula (IV), q=0, t=1, and A is a non-aromatic ring system, wherein one carbon atom is replaced by S, or Y is H or F, and E is phenyl which is either unsubstituted or substituted with Cl, F and/or $CF_3$ or $OCF_3$.

In another particularly preferred embodiment of the invention, in compounds of formula (I), of formula (Ia), of formula (III), or of formula (IV), q=1, t=1, and A is a non-aromatic ring system, wherein one carbon atom is replaced by S, or E and Y are substituted or unsubstituted phenylene and phenyl, respectively.

In further particularly preferred embodiment, in compounds of formula (I), of formula (Ia), of formula (III), or of formula (IV), D=O (thus m=1), $R^3$ is H (thus n=1), q=1, t=1, and E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and A is a non-aromatic ring system, wherein one carbon atom is replaced by S.

In further particularly preferred embodiment, in compounds of formula (I), of formula (Ia), of formula (III), or of formula (IV), D=O (thus m=1), n=0, q=1, t=1, and E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and A is a non-aromatic ring system, wherein one carbon atom is replaced by S.

In further particularly preferred embodiment, in compounds of formula (I), of formula (Ia), of formula (III), or of formula (IV), D=S (thus m=1), n=0, q=1, t=1, and E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and A is a non-aromatic ring system, wherein one carbon atom is replaced by S.

In formula (I), of formula (Ia), of formula (II), of formula (III), or of formula (IV) q is 0 or 1. If q is 1 and n is 0 or 1, D is preferably O (thus m=1).

In particular preferred embodiments of the invention, in compounds of formula (I), t=1, $Z^1$=O, $Z^2$=O (thus r=1), X=CO, E is phenylene which is either unsubstituted or substituted with Cl, F and/or $CF_3$ or $OCF_3$, and Y is phenyl which is also either unsubstituted or substituted with methoxy, ethoxy, Cl, F and/or $CF_3$ or $OCF_3$, and. A is a five membered aromatic ring system and $R^2$ together with the nitrogen atom which is attached to $R^8$ form a 6 membered heterocyclic ring with the proviso that $R^2$ is —[$CH_2$]$_8$ and $R^8$ is absent; and A is a five membered carbocylic ring system.

In particular preferred embodiments of the invention, in compounds of formula (I), t=1, $Z^1$=O, $Z^2$=O (thus r=1), X=CO, and E is phenylene which is either unsubstituted or substituted with Cl, F and/or $CF_3$ or $OCF_3$, and Y is H or F, and $R^2$ togehter with the nitrogen atom which is attached to $R^8$ form a 6 membered heterocyclic ring with the proviso that $R^2$ is —[$CH_2$]$_8$ and $R^8$ is absent; and A is a five membered carbocylic ring system.

The compounds of the formula (I), of formula (Ia), of formula (III), or of formula (IV), to be used according to the invention can form salts with inorganic or organic acids or bases.

Examples of such salts are, for example, alkali metal salts, in particular sodium and potassium salts, or ammonium salts.

The compounds of the present invention can be used for a variety of human and animal diseases, preferably human diseases, where inhibition of the pyrimidine metabolism is, beneficial. Such diseases are:

fibrosis, uveitis, rhinitis, asthma or arthropathy, in particular, arthrosis all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, serious forms of allergy, graft versus host and host versus graft rations, alzheimer's or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and lupus erythematoidis, ulcerative colitis, Morbus Crohn, inflammatory bowel disease, as well as other chronic inflammations, chronic diarrhea;

dermatological disorders such as psoriasis progressive retinal atrophy all kinds of infections including opportunistic infections.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the development of immunomodulatory and anti-inflammatory medicaments or, more generally, for the treatment of diseases where the inhibition of the pyrimidine biosynthesis is beneficial.

The compounds of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach; coloretal, genitourinary, gastrointestinal, skin, pancreatic, brain, uterine, colon, head and neck, and ovarian, melanoma, astrocytoma, small cell lung cancer, glioma, and squameous cell carcinoma, sarcomas as Kaposi's sarcoma and osteosarcoma), treatment of disorders involving T-cells such as aplastic anemia and DiGeorge syndrome, Graves' disease.

Leflunomide, was previously found to inhibit HCMV replication in cell culture. Ocular herpes is the most common couse of infectious blindness in the developed world. There are about 50.000 cases per year in the US alone, of which 90% are recurences of initial infections. Recurrences are treated with antivirls and corticosteroids. Cytomegalovirus another herpes virus is a common couse of retinal damage and blindness in patients with aids. The compounds of the present invention can be used alone or in combination with other antiviral compounds such as Ganciclovir and Foscarnet to treat such diseases.

The compounds of the preset invention can ether be used for diseases that are caused by protozoal infestations in humans and animals. Such veterinary and human pathogenic protozoas are preferably intracellular active parasites of the phylum Apicomplexa or Sarcomastigophora, especially Trypanosoma, Plasmodia, Leishmania, Babesia and Theileria, Cryptosporidia, Sacrocystida, Amoebia, Coccidia and Trichomonadia. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosparidium parvum*, Chargas' disease, caused by *Trypanosoma cruzi*, sleeping sickness, caused by *Typanosoma brucei* rhodesiense or gambiense, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Typanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing european bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and Isospora species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for viral infections or other infections caused for instance by *Pneumocystis carinii*.

The compounds of formula (I), formula (Ia), of formula (III), or of formula (IV), and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of the formula (I), formula (Ia), of formula (III), or of formula (IV), or a silt thereof, in addition to customary pharmaceutically innocuous excipients and additives. The compounds of formula (I), of formula (Ia), of formula (III), or of formula (IV), can also be administered in form of their salts, which are obtainable by reacting the respective compounds with physiologically acceptable acids and bases.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g., in the form of injections or infusions, or percutaneously, e.g. in the form of ointments, creams or tinctures.

In addition to the active compounds of formula (I), of formula (Ia), of formula (III), or of formula (IV) the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula (I), of formula (Ia), of formula (III), or of formula (IV) or their pharmacologically acceptable salts and also other therapeutically active substances.

Thus, the compounds of the present invention can be used in the form of one substance alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 500 mg, preferably 50 to 500 mg, per human individual is appropriate in the case of the oral administration which is, the preferred form of administration according to the invention. In the case of other administration forms too, the daily dose is in similar ranges.

The compounds of formula (I), of formula (Ia), of formula (III), or of formula (IV) can also be used in the form of a precursor (prodrug) or a suitably modified form, that releases the active compound in vivo. Such precursors such as the preferred embodiments of $R^6$ or $R^1$ can be obtained for example by masking the free acid group with an ester group, which is then in turn transformed into the free acid group in vivo [F. W. Sum et. al. Bioorg. & Med. Chem. Lett. 9 (1999), 1921–1926; Ada Rephaeli et. al. Drug Development Research 50 (2000) 379–391; H. Ishikawa, Current Med. Chem. 6 (1999), 575–597]. Further precursors for the preferred embodiments of $R^6$ or $R^1$ is tetrazole, another metabolism-resistant isosteric replacements for the carboxylic acid group as described by J. Herr, Bioorg. & Med. Chem. Lett. 10 (2002), 3379–3393. Other precursors for the preferred embodiments of $R^5$ can be obtained for example by masking the amidine with an hydroxy group, which is then in turn transformed into the fire amidine in vivo [R. M. Scarborough, J. Med. Chem. 43, 19, (2000), 3454–3473].

EXAMPLES

1. Synthesis of cyclopent-1-ene-1,2,3-tricarboxylic acid monoamide and cyclopent-1-ene-1,2,5-tricarboxylic acid monoamide and derivatives A solution of cyclopent-1-ene-1,2-dicarboxylic acid methylester (1 eq, 1 mmol) dissolved in chloroform (3 ml) was heated at 70° C. under reflux irradiated with a 300 W sunlamp. N-bromsuccinimide (1.05 eq) was added in small portions under heating and irradiating over a period of 3 h. Heating and irradiation was continued for 2 h. After the reaction was finished (monitored by TLC) the mixture was cooled to room temperature, the solvent was removed in vacuum and the residue was purified by flash chromatographie using a hexane/ethylacetat gradient to give 3-Bromo-cyclopent-1-ene-1,2-dicarboxylic acid dimethyl ester in a yield between 60 and 80%.

3-Bromo-cyclopent-1-ene-1,2-dicarboxylic acid dimethyl ester was dissolved in acetonitril under inert conditions. Tetraethylammoniumcyanide (1.1 eq) was added in one portion. The mixture was stirred under inert gas until the reaction was finished (2 h monitored by TLC). The solvent was removed in vacuum and the residue was purified by flash chromatographie using a hexane/ethylacetat gradient to give 3-Cyano-cyclopent-1-ene-1,2-dicarboxylic acid dimethyl ester in 25% yield.

3-Cyano-cyclopent-1-ene-1,2-dicarboxylic acid dimethyl ester was dissolved in concentrated hydrochloric acid and refluxed for 4 h. The solvent was removed in vacuum. The resulting residue was purified by HPLC to give the product in 50% yield Cyclopent-1-ene-1,2,3-tricarboxylic acid was suspended in acetic anhydride and stirred for 8 h. The solvent was removed in vacuum and the resulting crude product was used without faker purification.

The resulting anhydrid (1 eq, 1 mmol) was dissolved in dichlormethane (3 ml) and the 4-aminobiphenyl derivate (1 eq, 1 mmol) was add to the solution. After stirring for 18 h at room temperatures the solvent was removed in vacuum the residue was purified by HPLC to give the cyclopent-1-ene-1,2,3-tricarboxylic acid monoamide and cyclopent-1-ene-1,2,5-tricarboxylic acid monoamide derivative.

2. Synthesis of cyclopent-1-ene-1,2-dicarboxylic acid 2-hydroxyamide 1-monoamide derivate A solution of cyclopent-1-ene-1,2-dicarboxylic acide monoamide (1 equ, 1 mmol) and TBTU (1 eq, 1 mmol) in dimethylformamide (3 ml) was stirred for 10 minutes at room temperature. Afterwards O-t-butylhydroxylamine hydrochloride (1 eq, 1 mmol) and N,N-diisopropylethylamine (1 eq, 1 mmol) was added and the solution was sired for 18 h at room temperatures. The solvent was removed in vacuum and the residue was purified by HPLC to give the pure product.

3. Synthesis of 3-hydroxy-cyclopentene-dicarboxylic acide-monoamide and 5-hydroxy-cyclopentene-dicarboxylic acide-monoamide A solution of 5,6-dihydro-4H-cyclopenta[c]furan-1,3-dione (1 eq, 1 mmol) in chloroform (3 ml) was heated at 70° C. under reflux. During the solution was irradiated with a 300W sunlamp, N-bromosuccinimide (1,2 eq, 1,2 mmol) was added in small portions. After 1 h the solution was cooled to room temperature, and the solvent was removed in vacuum. The residue was dissolved in dichloromethane (3 ml) and a 4-amino-biphenyl-derivate (1 eq, 1 mmol) was added. The solution was stirred at room temperature for 18 h. The solvent was removed in vacuum and the residue was dissolved in acetonitrile/water and purified by HPLC to give the 3-hydroxy-cyclopentene-dicarboxylicacide-monoamide and 5-hydroxy-cyclopentene-dicarboxylic acide-monoamide 4. Synthesis cylopentenedicarboxylic acid 2-monoamide 1-alkyl ester 5,6-Dihydro-4H-cyclopenta[c]furan-1,3-dione (1 eq, 1 mmol) was dissolved in the respective alcohol (3 ml) and stirred for 18 h at room temperature to optain the desired mono alkyl ester. Afterwards the solvent was removed in vakuum and the residue was used without further purification in the next step.

Cyclopent-1-ene-1,2-dicarboxylic acid monoalkyl ester (1 eq, 1 mmol) was dissolved in dichlormethylen and thionylchlorid (1,2 eq, 1,2 mmol) was add dropwise under ice cooling. The mixture was stirred for 1 h at room temperature and the solvent was removed at vacuum. This product was also used without a purification in the next step.

2-Chlorocarbonyl-cyclopent-1-enecaroxylic acid alkyl ester was solved in dichlormethylen (3 ml) and the respective 4-amino-biphenyl was added in one portion. The mixture was stirred for 18 h at room temperature and afterwards the solvent was removed at vakuum. The product was purified by recristallisation.

Example 1

3-(3-Fluoro-3'-methoxy-biphenyl-4-ylcarbamoyl)-cyclopent-2-ene-1,2-dicarboxylic acid LC/(+)-ESI-MS: m/z=400 [M+H]$^+$

Example 2

2-(3-Fluoro-3'-methoxy-biphenyl-4-ylcarbamoyl)-cyclopent-1-ene-1,3-dicarboxylic acid LC/(+)-ESI-MS: m/z=400 [M+H]$^+$

Example 3

2-(3-Fluoro-3'-methoxy-biphenyl 4-ylcarbamoyl)cyclopent-1-enecarboxylic acid methyl esterLC/(+)-ESI-MS: m/z=370 [M+H]$^+$

Example 4

Cyclopent-1-ene-1,2-dicarboxylic acid 1-[(3-fluoro-3'-methoxy-biphenyl-4-yl)amide]2-hydroxyamide LC/(+)-ESI-MS: m/z 371 [M+H]$^+$

Example 5

3-Hydroxy-2-(2,3,5,6-tetrafluoro-3'-trifluoromethoxy-biphenyl-4-ylcarbamoyl)cyclopent-1-enecarboxylic acid LC/(+)-ESI-MS: m/z=480 [M+H]$^+$

Example 6

5-Hydroxy-2-(2,3,5,6-tetrafluoro-3'-trifluoromethoxy-biphenyl-4-ylcarbamoyl)-cyclopent-1-enecarboxylic acid LC/(+)-ESI-MS: m/z=480 [M+H]$^+$

Example 7

2-(3'-Ethoxy-3,5-difluoro-biphenyl-4-ylcarbamoyl)-3-hydroxy-cyclopent-1-enecarboxylic acid LC/(+)-ESI-MS: m/z 404 [M+H]$^+$

Example 8

2-(3'-Ethoxy-3,5-difluoro-biphenyl-4-ylcarbamoyl)-5-hydroxy-cyclopent-1-enecarboxylic acid LC/(+)-ESI-MS: m/z=404 [M+H]$^+$

Example 9

2-(1',3'-di-methoxy-3,5-difluoro-biphenyl-4-ylcarbamoyl)-3-hydroxy-cyclopent-1-enecarboxylic acid LC/(+)-ESI-MS: m/z 420 [M+H]$^+$

Example 10

2-(1',3'-di-methoxy-3,5-difluoro-biphenyl-4-ylcarbamoyl)-5-hydroxy-cyclopent-1-enecarboxylic acid LC/(+)-ESI-MS: m/z 420 [M+H]$^+$

Example 11

3-Hydroxy-2-(3,5,2'-trifluoro-biphenyl-4-ylcarbamoyl)-cyclopent-1-enecarboxylic acid LC/(+)-ESI-MS: m/z 378 [M+H]$^+$

Example 12

5-Hydroxy-2-(3,5,2'-trifluoro-biphenyl-4-ylcarbamoyl)-cyclopent-1-enecarboxylic acid LC/(+)-ESI-MS: m/z=378 [M+H]$^+$

Example 13

2-(2-Chloro-2'-methoxy-biphenyl-4-ylcarbamoyl)$_3$-hydroxy-cyclopent-1-enecarboxylic acid LC/(+)-ESI-MS: m/z=388 [M+H]$^+$

Example 14

2-(2-Chloro-2'-methoxy-biphenyl-4-ylcarbamoyl)-5-hydroxy-cyclopent-1-enecarboxylic acid LC/(+)-ESI-MS: m/z=388 [M+H]$^+$

Example 15

2-(2'-Chloro-3,5-difluoro-biphenyl-4-ylcarbamoyl)-3-hydroxy-cyclopent-1-enecarboxylic acid LC/(+)-ESI-MS: m/z 394 [M+H]$^+$

Example 16

2-(2'-Chloro-3,5-difluoro-biphenyl-4-ylcarbamoyl)-5-hydroxy-cyclopent-1-enecarboxylic acid LC/(+)-ESI-MS: m/z=394 [M+H]$^+$

Example 17

2-(3-Fluoro-3'-methoxy-biphenyl-4-ylcarbamoyl)-3-hydroxy-cyclopent-1-enecarboxylic acid LC/(+)-ESI-MS: m/z=372 [M+H]$^+$

Example 18

2-(3-Fluoro-3'-methoxy-biphenyl-4-ylcarbamoyl)-5-hydroxy-cyclopent-1-enecarboxylic acid LC/(+)-ESI-MS: m/z=372. [M+H]$^+$ 3. Inhibition Assay of DHODH Activity The standard assay mixture contained 50 µM decyclo ubichinone, 100 µM dihydroorotate, 60 µM 2,6-dichloroindophenol, as well as 20 mU DHODH. The volume activity of the recombinant enzyme used was 30 U/ml. Measurements were conducted in 50 mM TrisHCl (150 mM KCl, 0.1% Triton X-100, pH 8.0) at 30° C. in a final volume of 1 ml. The components were mixed, and the reaction was started by adding dihydroorotate. The course of reaction was followed by spectrophotometrically measuring the decrease in absorption at 600 nm for 2 min.

Inhibitory studies were conducted in a standard assay with additional variable amounts of inhibitor. For the determination of the IC$_{50}$ values (concentration of inhibitor required for 50% inhibition) at least five different inhibitor concentrations were applied.

These investigations were carried out with recombinant human as well as with recombinant murine DHODH provided by Prof. M. Löffler, Marburg, Germany [M. Löffler, Chem. Biol. Interact. 124, (2000), 61–76].

Examples 5, 6, 7, 8, 11, 12, 13, 14, 15, 16, 17 and 18 showed $IC_{50}$-values (human DHODH) of <1 μM. Examples 9 and 10 showed $IC_{50}$-values (human DHODH) of <5 μM. Examples 1, 2, 3 and 4 showed $IC_{50}$-values (human DHODH) of >5 μM.

The invention claimed is:

1. A compound of the general formula (I) or a salt or a physiologically functional derivative thereof:

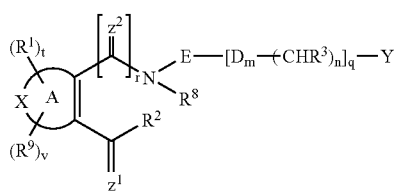

(I)

wherein

A is a non-heterocyclic non-aromatic ring system containing 4 to 8 carbon atoms, wherein the ring system comprises at least one double bond and wherein one or more of the carbon atoms in the ring represented X may optionally be carbonyl (C=O);

D is O, S, $SO_2$, $NR^4$ or $CH_2$;

$z^1$ and $z^2$ are independent from each other O, S, or $NR^5$;

$R^1$ is independently —$CO_2R''$, —$SO_3H$, —$CONR*R''$, —$CR''O$, —$SO_2$—$NR*R''$, —$NO_2$, —$SO_2$—$R''$, —SO—$R*$, —CN, alkoxy, —OH, —SH, alkylthio, —$NR''$—$CO_2$—$R'$, —$NR''$—CO—$R*$, —$NR''$—$SO_2$—$R'$, —O—CO—$R*$, —O—$CO_2$—$R*$, —O—CO—$NR*R''$; cycloalkyl, alkylamino, hydroxyalkylamino, aryl, or heteroaryl;

$R^9$ is independently H, halogen, haloalkyl, haloalkyloxy or alkyl;

$R*$ is independently H, alkyl, cycloalkyl, aminoalkyl, alkoxy, —OH, —SH, alkylthio, hydroxyalkyl, haloalkyl, haloalkyloxy, aryl or heteroaryl;

$R'$ is independently H, —$CO_2R''$, —$CONHR''$, —$CR''O$, —$SO_2NR''$, —$NR''$—CO-haloalkyl, —$NO_2$, —$NR''$—$SO_2$-haloalkyl, —$NR''$—$SO_2$-alkyl, —$SO_2$-alkyl, —$NR''$—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl arylalkyl or heteroaryl;

$R''$ is independently hydrogen, haloalkyl, hydroxyalkyl, alkyl, cycloalkyl, aryl, heteroaryl or aminoalkyl;

$R^2$ is H, $OR^6$, or $NHR^7$;

$R^3$ is H, alkyl, cycloalkyl, aryl, arylalkyl, alkoxy, O-aryl, O-cycloalkyl, halogen, aminoalkyl, alkylamino, hydroxylamino, hydroxylalkyl, haloalkyl, haloalkyloxy, heteroaryl, alkylthio, S-aryl, or S-cycloalkyl;

$R^4$ is H, alkyl, cycloalkyl, aryl, or heteroaryl;

$R^5$ is H, OH, alkoxy, O-aryl, alkyl, or aryl;

$R^6$ is H, alkyl, cycloalkyl, aryl, heteroaryl, arylalkyl, alkylaryl, alkoxyalkyl, acylmethyl, (acyloxy)alkyl, non-symmetrical (acyloxy)alkyldiester, or dialkylphosphate;

$R^7$ is H, alkyl, aryl, alkoxy, O-aryl, cycloalkyl, or O-cycloalkyl;

$R^8$ is hydrogen or alkyl;

E is an alkyl or cycloalkyl group which is substituted by $[D_m$-$(CHR_3)_n]_qY$ or a monocyclic or polycyclic substituted or unsubstituted ring system which contains at least one aromatic ring;

Y is hydrogen, halogen, haloalkyl, haloalkyloxy, alkyl, cycloalkyl, a monocyclic or polycyclic substituted or unsubstituted ring system and which contains at least one aromatic ring or

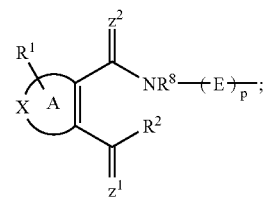

m is 0 or 1;
n is 0 or 1;
p is 0 or 1;
r is 0 or 1;
q is 0 or 1;
t is 1 to 3; and
v is 0 to 3.

2. A compound of the general formula (Ia) or a salts or a physiologically functional derivatives thereof,

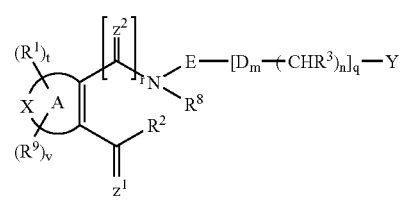

(Ia)

wherein

A is a non-heterocyclic non-aromatic ring system containing 4, 5, 6, 7 or 8 carbon atoms, wherein the ring system comprises at least one double bond and wherein one or more of the carbon atoms in the ring represented X may be carbonyl (C=O);

D is O, S, $SO_2$, $NR^4$, or $CH_2$;

$z^1$ and $z^2$ are independent from each other O, S, or $NR^5$;

$R^1$ is independently H, halogen, haloalkyl, haloalkyloxy —$CO_2R''$, —$SO_3H$, —OH, —$CONR*R''$, —$CR''O$, —$SO_2$—$NR*R''$, —$NO_2$, —$SO_2$—$R''$, SO—$R*$, —CN, alkoxy, alkylthio, aryl, —$NR''$—$CO_2$—$R'$, —$NR''$—CO—$R*$, —$NR''$—$SO_2$—$R'$, —O—CO—$R*$, —O—$CO_2$—$R*$, —O—CO—$NR*R''$; cycloalkyl, alkylamino, hydroxyalkylamino, —SH, heteroaryl, or alkyl;

$R*$ is independently H, alkyl, cycloalkyl aminoalkyl, alkoxy, —OH, —SH, alkylthio, hydroxyalkyl, haloalkyl, haloalkyloxy, aryl or heteroaryl;

$R'$ is independently H, —$CO_2R''$, —$CONHR''$, —$CR''O$, —$SO_2NR''$, —$NR''$—CO-haloalkyl, —$NO_2$, —$NR''$—$SO_2$-haloalkyl, —$NR''$—$SO_2$-alkyl, —$SO_2$-alkyl, —$NR''$—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl arylalkyl or heteroaryl;

R" is independently hydrogen, haloalkyl, hydroxyalkyl, alkyl, cycloalkyl, aryl, heteroaryl or aminoalkyl;

$R^2$ is NHOH or $R^2$ together with the nitrogen atom which is attached to $R^8$ form a 5 or 6 membered heterocyclic ring with the proviso that $R^2$ is $-[CH_2]_8$ and $R^8$ is absent;

$R^3$ is H, alkyl, cycloalkyl, aryl, alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl, or haloalkyl;

$R^4$ is H, alkyl, cycloalkyl, aryl or heteroaryl;

$R^5$ is H, OH, alkoxy, O-aryl, alkyl or aryl;

$R^8$ is hydrogen, or alkyl;

E is an alkyl or cycloalkyl group which is substituted by $[D_m-(CHR_3)_n]_q Y$ or a monocyclic or polycyclic substituted or unsubstituted ring system which contains at least one aromatic ring;

Y is hydrogen, halogen, haloalkyl, haloalkyloxy, alkyl cycloalkyl, a monocyclic or polycyclic substituted or unsubstituted ring system which contains at least one aromatic ring or

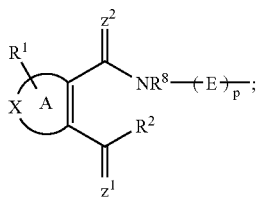

m is 0 or 1;
n is 0 or 1;
p is 0 or 1;
r is 0 or 1;
q is 0 or 1;
s is 0 to 2; and
t is 0 to 3;

with the proviso at the following compounds are excluded:

compounds wherein ring A is an unsubstituted carbocycle containing six carbon atoms and one double bond between the $CZ^1$ and $CZ^2$-substituents, $z^1=z^2=O$, and s is 0; 1,3,5-Tribenzyl-2,4,6-trioxopyrrolo[3,4-d]imidazole, 1,3-Dibenzyl-5-(4-methoxy-benzyl)-2,4,6-trioxopyrrolo[3,4-d]imidazole, 1,3-Bis-(methoxybenzyl)-5-benzyl-2,4,6-trioxopyrrolo[3,4-d]imidazole, and 1,3-Tris-(4-methoxybenzyl)-2,4,6-trioxo-pyrrolo[3,4-d]imidazole.

3. A compound of the general formula (IV) or a salts or physiologically functional derivative thereof,

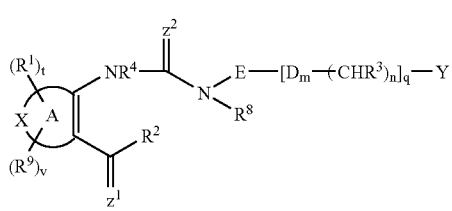

(IV)

wherein

A is a non-heterocyclic, non-aromatic ring system containing 4, 5, 6, 7 or 8 carbon atoms, wherein the ring system comprises at least one double bond and wherein one or more of the carbon atoms in the ring represented by X may be carbonyl (C=O);

D is O, S, $SO_2$, $NR^4$, or $CH_2$;

$z^1$ and $z^2$ are independent from each other O, S, or $NR^5$;

$R^1$ is independently H, halogen, haloalkyl, haloalkyloxy $-CO_2R"$, $-SO_3H$, $-OH$, $-CONR*R"$, $-CR"O$, $-SO_1NR*R"$, $-NO_2$, $-SO_2-R"$, $-SO-R*$, $-CN$, alkoxy, alkylthio, aryl, $-NR"-CO_2-R'$, $NR"-CO-R*$, $-NR"-SO_2-R'$, $-O-CO-R*$, $-O-OC_2-R*$, $-O-CO-NR*R"$; cycloalkyl, alkylamino, hydroxyalkylamino, heteroaryl, $-SH$; or alkyl;

R* is independently H, alkyl, cycloalkyl, aminoalkyl, alkoxy, $-OH$, $-SH$, alkylthio, hydroxyalkyl, haloalkyl, haloalkyloxy, aryl or heteroaryl;

R' is independently H, $-CO_2R"$, $-CONHR"$, $-CR"O$, $-SO_2NR"$, $-NR"-CO$-haloalkyl, $-NO_2$, $-NR"-SO_2$-haloalkyl, $-NR"-SO_2$-alkyl, $-SO_2$-alkyl, $-NR"-CO$-alkyl, $-CN$, alkyl, cycloalkyl, aminoalkyl, alkylamino, alkoxy, $-OH$, $-SH$, alkylthio, hydroxyalkyl, hydroxyalkylamino, halogen, haloalkyl, haloalkyloxy, aryl arylalkyl or heteroaryl;

R" is independently hydrogen, haloalkyl, hydroxyalkyl, alkyl, cycloalkyl, aryl, heteroaryl or aminoalkyl;

$R^2$ is H or $OR^6$, $NHR^7$, $NR^7OR^7$ or $R^2$ together with the nitrogen atom which is attached to $R^8$ form a 6 membered hetercyclic ring with the proviso that $R^2$ is $-[CH_2]_8$ and $R^8$ is absent;

$R^3$ is H, alkyl, cycloalkyl, aryl, alkoxy, O-aryl; O-cycloalkyl, halogen, aminoalkyl, alkylamino, hydroxylamino, hydroxylalkyl, haloalkyloxy, heteroaryl alkylthio, S-aryl; S-cycloalkyl, arylalkyl, or haloalkyl;

$R^4$ is H, alkyl, cycloalkyl aryl or heteroaryl;

$R^5$ is H, OH, alkoxy, O-aryl, alkyl or aryl;

$R^6$ is H, alkyl, cycloalkyl, aryl, arylalkyl, heteroaryl, alkylaryl, alkoxyalkyl, acylmethyl, (acyloxy)alkyl, non-symmetrical (acyloxy)alkyldiester, or dialkylphosphate;

$R^7$ is H, OH, alkyl, aryl, alkoxy, O-aryl, cycloalkyl or O-cycloalkyl;

$R^8$ is hydrogen, or alkyl;

E is an alkyl or cycloalkyl group which is substituted by $[D_m-(CHR_3)_n]_q Y$ or a monocyclic or polycyclic substituted or unsubstituted ring system which contains at least one aromatic ring;

Y is hydrogen, halogen, haloalkyl, haloalkyloxy, alkyl, cycloalkyl, a monocyclic or polycyclic substituted or unsubstituted ring system which contains at least one aromatic ring or

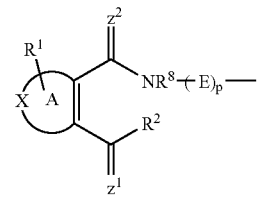

m is 0 or 1;
n is 0 or 1;
p is 0 or 1;
q is 0 or 1;
s is 0 to 2; and
t is 0 to 3;

with the proviso that the following compounds are excluded: 5,5-Dimethyl-4-phenyl-2-(3-phenyl-ureido-4,5-dihydro-furan-3-carboxylic acid methyl ester, 2[3-(4-Chlorophenyl-ureido)]-5,5-dimethyl-4-phenyl-4,5-dihydro-furan-3-carboxylic acid methyl ester, 2[3-(4-Methoxylphenyl-ureido)]-5,5-dimethyl-4-phenyl-4,5-dihydro-furan-3-carboxylic acid methyl ester, 2[3-(4-Methylphenyl-ureido)]-5,5-dimethyl-4-phenyl-4,5-dihydro-furan-3-carboxylic acid methyl ester, 2[3-(4-Nitrophenyl-ureido)]-5,5-dimethyl-4-phenyl-4,5-dihydro-furan-3-carboxylic acid methyl ester, 4-(4-Chlorophenyl)-5,5-dimethyl-2-(3-phenyl-ureido)-4,5-dihydro-furan-3-carboxylic acid methyl ester, 4-(4-Chlorophenyl)-2[3-(4-chlorophenyl-ureido)]-5,5-dimethyl-4,5-dihydro-furan-3-carboxylic acid methyl ester, 4-(4-Chlorophenyl)-2[3-(4-nitrophenyl-ureido)]-5,5-dimethyl-4,5-dihydro-furan-3-carboxylic acid methyl ester, 4-(4-Chlorophenyl)-2[3-(4-methoxyphenyl-ureido)]-5,5-dimethyl-4,5-dihydro-furan-3-carboxylic acid methyl ester, or 4-(4-Chlorophenyl)-2[3-(4-nitrophenyl-ureido)]-5,5-dimethyl-4,5-dihydro-furan-3-carboxylic acid methyl ester.

4. A pharmaceutical composition comprising:
the compound as defined in claim 1; and
a pharmaceutically acceptable diluent or carrier.

5. A pharmaceutical composition comprising:
the compound as defined in claim 2; and
a pharmaceutically acceptable diluent or carrier.

6. A method for treating a disease associated with the expression of dihydroorotate dehydrogenase ("DHODHD") comprising administering an amount of the compound of claim 1 effective to inhibit the activity of DHODH to a subject in need thereof.

7. A method for treating a disease associated with the expression of DHODH comprising administering an amount of the compound of claim 2 effective to inhibit the activity of DHODH to a subject in need thereof.

8. The method of claim 6, wherein the disease is selected from the group consisting of rheumatism, an acute immunological disorder, an autoimmune disease, a disease caused by malignant cell proliferation, an inflammatory disease, a disease that is caused by a protozoal infestation, a disease that is caused by a viral infection, *Pneurnocystis carinii*, fibrosis, uveitis, rhinitis, asthma and athropathy.

9. The method of claim 6, comprising administering a compound of the general formula (I) or a salt thereof.

10. The compound of claim 1, which is compound of the general formula (I) in free form.

11. The compound of claim 1, which is a salt of a compound of general formula (I).

12. The compound of claim 1, which is a physiologically functional derivative of a compound of general formula (I).

13. The compound of claim 1, wherein ring A contains five carbon atoms.

14. The compound of claim 1, wherein ring A contains a single double bond between the carbon atoms carrying substituents $Cz^1$ and $Cz^2$.

15. The compound of claim 1, wherein ring A contains a single X group which is carbonyl (C=O).

16. The compound of claim 1, wherein none of the carbon atoms is replaced by X, which is carbonyl.

17. The compound of claim 1, wherein $R^1$ is OH, $OCH_3$, SH, $CO_2H$, $SO_3H$ or tetrazole.

18. The compound of claim 1, wherein $R^9$ is H.

19. The compound of claim 1, wherein $R^2$ is OH or $OR^6$.

20. The compound of claim 1, wherein $R^8$ is H or methyl.

21. The compound of claim 1, wherein Y is optionally substituted phenyl.

22. The compound of claim 1, wherein D is S or O and m=1.

23. The compound of claim 1, wherein $z^1$ and $z^2$ are both O.

* * * * *